United States Patent [19]

Grisar et al.

[11] Patent Number: 5,721,233

[45] Date of Patent: Feb. 24, 1998

[54] DERIVATIVES OF 2,3-DIHYDRO BENZOFURANOLS

[75] Inventors: J. Martin Grisar, Wissembourg; Margaret A. Petty, Strasbourg, both of France; Frank Bolkenius, Kehl, Germany

[73] Assignee: Merrell Pharmaceuticals Inc., Cincinnati, Ohio

[21] Appl. No.: 318,633

[22] PCT Filed: Mar. 10, 1993

[86] PCT No.: PCT/US93/02107

§ 371 Date: Dec. 22, 1994

§ 102(e) Date: Dec. 22, 1994

[87] PCT Pub. No.: WO93/20057

PCT Pub. Date: Oct. 14, 1993

[30] Foreign Application Priority Data

Apr. 6, 1992 [EP] European Pat. Off. ............ 92400956

[51] Int. Cl.$^6$ ............. A61K 31/535; A61K 31/495; C07D 405/06; C07D 413/06

[52] U.S. Cl. ............. 514/233.5; 514/253; 514/278; 514/320; 514/409; 514/422; 514/462; 514/469; 544/70; 544/153; 544/230; 544/295; 544/376; 546/15; 546/196; 548/407; 548/525; 549/467

[58] Field of Search ............... 544/153, 295, 544/376, 70, 230; 546/196, 15; 548/525, 407; 549/462, 467, 468, 470; 514/233.5, 253, 320, 409, 422, 462, 469, 470, 278

[56] References Cited

U.S. PATENT DOCUMENTS

| | | | |
|---|---|---|---|
| 3,419,560 | 12/1968 | Bernstein et al. | 544/401 |
| 3,947,473 | 3/1976 | Scott et al. | 549/405 |
| 4,153,796 | 5/1979 | Hoehn | 546/120 |
| 4,214,081 | 7/1980 | Krapcho | 544/165 |
| 4,237,162 | 12/1980 | Kabbe et al. | 514/455 |
| 4,321,270 | 3/1982 | Sundeen | 546/120 |
| 4,617,317 | 10/1986 | Bennet | 514/458 |
| 4,694,090 | 9/1987 | Shiono et al. | 549/407 |
| 4,728,650 | 3/1988 | Eziri et al. | 514/253 |
| 4,857,516 | 8/1989 | Terao et al. | 514/100 |
| 4,975,457 | 12/1990 | Rupprecht et al. | 514/469 |
| 5,504,213 | 4/1996 | Fischer et al. | 548/253 |
| 5,552,552 | 9/1996 | Ohkawa et al. | 546/196 |

FOREIGN PATENT DOCUMENTS

| | | |
|---|---|---|
| 0036169 | 9/1981 | European Pat. Off. |
| 0236120 | 9/1987 | European Pat. Off. |
| 0281261 | 9/1988 | European Pat. Off. |
| 0293078 | 11/1988 | European Pat. Off. |
| 0345593 | 12/1989 | European Pat. Off. |
| 0369083 | 5/1990 | European Pat. Off. |
| 0369874 | 5/1990 | European Pat. Off. |
| 0387771 | 9/1990 | European Pat. Off. |
| 0413668 | 2/1991 | European Pat. Off. |
| 0483772 | 5/1992 | European Pat. Off. |
| 0550337 | 7/1993 | European Pat. Off. |
| 0536036 | 9/1993 | European Pat. Off. |
| 2634766 | 2/1990 | France. |
| 9320058 | 10/1993 | WIPO. |
| 9320059 | 10/1993 | WIPO. |

OTHER PUBLICATIONS

Shiono et al, *Chemical Abstracts*, vol. 105, No. 226358 (1986) (Abstract for JP 61,148,173, Jul. 5, 1986).
Shiono et al, *Chemical Abstracts*, vol. 105, No. 197188 (1986) (Abstract for JP 61,148120, Jul. 5, 1986).
Matsuo et al, *Chemical Abstracts*, vol. 114, No. 81586 (1990) (Abstract for JP 02,215,778, Aug. 28, 1990).
Hirose et al, *Chemical Abstracts*, vol. 81, No. 135855 (1974).
Beach et al, *Archives of Biochemistry and Biophysics*, 297, pp. 258–264 (Aug. 15, 1992).
Ciattini et al, *J. Heterocyclic Chem.* 19 pp. 395–399 (1982).
*Advanced Organic Chemistry* by Jerry March (2nd Ed.), pp. 349–352, 361, 398–399, 1121 (1977).
Hirose et al, *Yakugaku Zasshi* 94 (8) pp. 905–912 (1974).
Burger, Medicinal Chemistry, 2nd Edition, Interscience Publishers, Inc., New York, (1960) pp. 72–88.
Akkerman et al., J. Chem. Soc., Perkin Trans. I, No. 9, Sep. 1979, pp. 2119–2124.
Unanue et al., Text Book of Immunology, Williams & Wilkins, Baltimore, 1984, pp. 289–294.
Koyama et al., Chemical Abstracts, vol. 111, No. 13, 115639T (1989).

*Primary Examiner*—Emily Bernhardt
*Attorney, Agent, or Firm*—Carolyn D. Moon

[57] ABSTRACT

Derivatives of 2,3-dihydro-5-benzofuranol, intermediates thereof, and processes useful for their preparation. These compounds are free radical scavengers and are useful in the treatment of conditions capable of being treated by free radical scavengers, such as stroke, nervous system trauma and reperfusion damage.

26 Claims, No Drawings

DERIVATIVES OF 2,3-DIHYDRO BENZOFURANOLS

This invention relates to certain derivatives of 2,3-dihydro-benzofuranol; to the intermediates and processes useful for their preparation, to their ability to manifest the property of being free radical scavengers, and to their end-use application in the treatment of disease conditions capable of being ameliorated by free radical scavengers such as, for example, stroke, nervous system trauma or reperfusion damage.

More specifically this invention relates to compounds of the formula

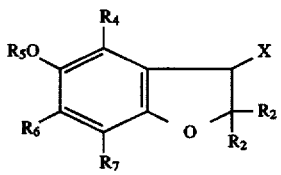
(1)

the stereoisomers and mixtures thereof, and their pharmaceutically acceptable salts thereof, wherein $R_2$ is $C_{1-4}$ alkyl or both $R_2$ moieties, when taken together with the carbon atom to which they are attached, form a $C_{5-6}$ cyclic hydrocarbyl moiety;

$R_4$ is $C_{1-6}$ alkyl;

$R_5$ is H or —C(O)R with R being H, or $C_{1-9}$ alkyl;

$R_6$ is $C_{1-6}$ alkyl;

$R_7$ is H or $C_{1-6}$ alkyl;

X is $COOR_8$, $CH_2OH$, halomethyl, C(O)A or —$CH_2A$;

A is —$NR_7R_9$, —$N^{\oplus}R_6R_6R_6$—$Q^{\ominus}$, pyrrolidino, piperidino morpholino, or

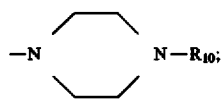

$R_8$ is H, $C_{1-6}$ alkyl, or —$(CH_2)_m$—A, with m being 2,3 or 4;

$R_9$ is H, $C_{1-4}$ alkyl,

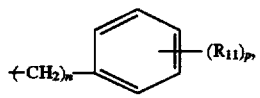

n is 1, 2, 3 or 4, p is 1,2 or 3;

$R_{10}$ is H, $C_{1-8}$ alkyl, $C_{1-6}$ alkenyl, $C_{4-6}$ cycloalkyl, cyclohexylmethyl, hydroxyalkyl ($C_{2-6}$), dihydroxyalkyl ($C_{3-6}$), $C_{2-9}$ acyloxyalkyl ($C_{2-6}$), $C_{1-4}$ alkoxyalkyl ($C_{1-6}$),

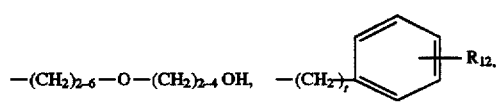

with t being 0, 1, or 2, or pyrimidinyl;

$R_{11}$ is H, $C_{1-4}$ alkoxy, $C_{1-4}$ alkyl or halogeno;

$R_{12}$ is ortho $C_{1-4}$ alkoxy, ortho $C_{1-4}$ alkyl or p-halo;

Q is a halogen$^{\ominus}$ or —$^{\ominus}SO_3R_1$ with $R_1$ being H, $C_{1-6}$ alkyl, aryl or aralkyl.

As used herein the term "alkyl" includes the straight and branched chain saturated aliphatic hydrocarbyl moieties having the indicated number of carbon atoms, preferably methyl or ethyl, but including others such as propyl, isopropyl, n-butyl and the like. The term —C(O)R includes moieties wherein R is B or a $C_{1-9}$ alkyl moiety, embracing, for example, formyl, methylcarbonyl, ethylcarbonyl, propylcarbonyl and the like. The —$NR_7R_9$ moieties include the amino and mono and di-substituted amines with $R_7$ and $R_9$ being as defined. The

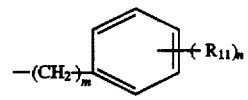

moiety includes benzyl, phenylethyl, phenylpropyl or phenylbutyl moieties; the phenyl moieties of which may bear 1,2 or 3 substituents represented by $R_{11}$ selected from the group consisting of $C_{1-4}$ alkoxy (preferably methoxy) $C_{1-4}$ alkyl (preferably methyl) or halogen (preferably chloro but including bromo and iodo). Similarly, mono and di-hydroxy substituted alkyl moieties are those moieties wherein the alkyl moiety can bear one or two OH groups (other than two hydroxy groups on one carbon atom), preferably moieties bearing a hydroxy group on a terminal carbon atom. $C_{2-9}$ acyloxy alkylene ($C_{2-6}$) are those compounds wherein the acyloxy moiety has 2 to 9 carbon atoms and the alkylene moiety has 2 to 6 carbon atoms such as exemplified by —$CH_2CH_2$—OC(O)$CH_3$. The —$C_{2-6}$ alkylene O—($CH_2)_{2-4}$ OH moieties have respectively a divalent 1–6 carbon atom moiety attached to an oxygen (O). The oxygen is also attached to a 1–4 carbon moiety terminating in a hydroxy moiety. One example is —$CH_2CH_2OCH_2CH_2CH_2OH$. Piperidino is illustrated by

and pyrrolidino

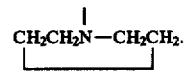

It is preferred that both $R_2$ alkyl moieties be the same (e.g. 2,2-dimethyl or 2,2-diethyl) but both need not be the same for any one compound. Similarly in those instances wherein A represents a tertiary amine both of $R_7$ and $R_9$ are preferably both the same, preferably both being methyl or ethyl, and when $R_9$ is other than H or alkyl, benzyl is preferred. The moiety —$N^{\oplus}R_6R_6R_6$. $Q^{\ominus}$ represents a quaternary ammonium moiety wherein Q includes all halides with chloro and bromo being preferred, and aryl includes phenyl or its alkylated derivatives with toluene as the preferred species and aralkyl includes benzyl or phenethyl and their alkylated derivatives.

The pharmaceutically acceptable salts include those acid addition salts derived by reaction with such acids as hydrochloric, hydrobromic, sulfuric, nitric or phosphoric acids and such organic carboxylic acids as acetic, propionic, glycolic, maleic, tartaric, citric, salicylic, 2-acetyloxybenzoic acids or organic sulfonic acids such as methanesulfonic 4-toluenesulfonic as naphthalensulfonic acids. Of course other acids well known to the pharmaceutical art may also be utilized.

The compounds of the present invention may exist in stereoisomeric forms, and the present invention is meant to include all stereoisomeric forms. The term "stereoisomer" is a general term for all isomers of individual molecules that differ only in the orientation of their atoms in space. It includes mirror image isomers (enantiomers), geometric (cis/trans) isomers, and isomers of compounds with more than one chiral center that are not mirror images of one another (diastereoisomers). It is recognized that certain stereoisomeric forms of the present invention may have properties which are superior to other stereoisomeric forms or mixtures thereof. These properties may be a better therapeutic response, better bioavailability, lower toxicity or any other desirable property. Standard methods of separation may be used to isolate the preferred stereoisomer.

In general, the compounds of formula I may be prepared by standard chemical processes and techniques analogously known in the art with the overall processes depicted in the following Reaction Schemes A, B and C.

REACTION SCHEME A

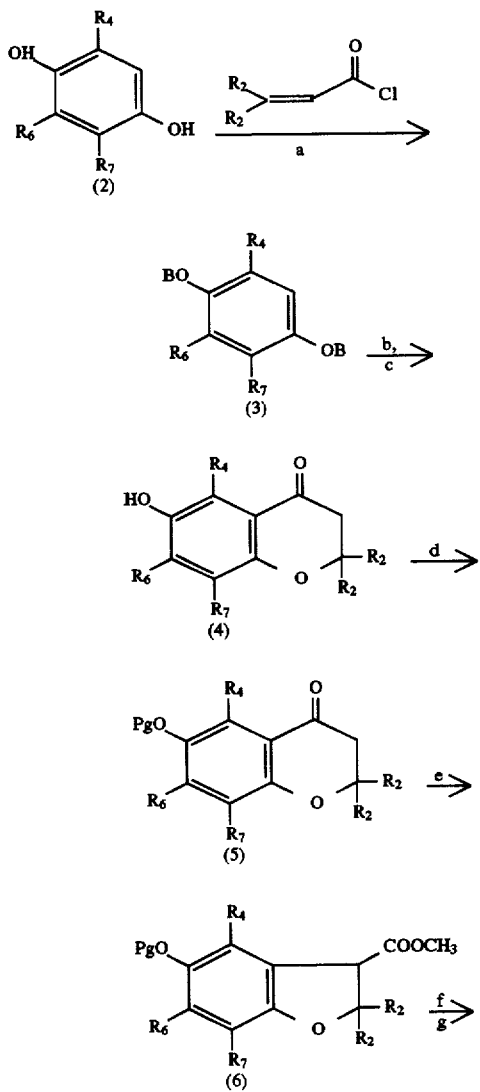

-continued
REACTION SCHEME A

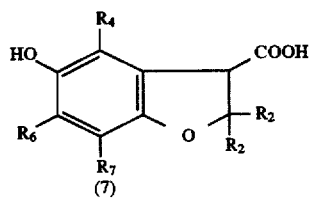

wherein $R_2, R_4, R_6$ and $R_7$ are as previously defined and B is

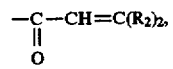

Pg is a protecting group, and including the oxygen to which it is attached forms an ester or an ether moiety, and is preferably para-nitrobenzoyl. Detailed aspects of the reaction steps (a) to (g) are summarized as follows: step (a) $C_6H_5CH_3$, reflux 1 hour; step (b) $AlCl_3$, 145°, 1.5 hour; step (C) 1N NaOH, 50% MeOH, reflux 1 hour; step (d) 4-$O_2$N—$C_6H_4COCl$, Pyridine, room temperature, 16 hours; step (e) thallium(III)($NO_3$)$_3$·3$H_2O$, ($CH_3O$)$_3$CH, MeOH, room temperature, 4 days; step (f) tetrahydrofuran, 2N NaOH, reflux 1 hour; step (g) 1N NaOH 50% MeOH, reflux 24 hours.

Using the Fries rearrangement of substituted acrylic acid diesters (3) of hydroquinones (2) gives 6-hydroxy-3,4-dihydro-1,2H-benzopyran-4-ones (4) as taught by N.V. Dudykina et al., *Khim. Gererotsikl. Soedin*, 1969, 434–439 (*Chem. Abstr.*, 1970, 72, 31545X). This reaction is carried out using a Lewis acid, preferably anhydrous aluminum chloride, at elevated temperatures, preferably at 120°–150° C., usually without a solvent. 3,3-Dimethyl, diethyl, tetramethylene and pentamethylene acrylic acid esters are preferably employed for this reaction and the hydroquinone is a 2,3-dialkyl or a 2,3,6-trialkyl substituted hydroquinone, the alkyl preferably being methyl. Only a few examples of the ring-contraction reaction of 3,4-dihydro-1(2H)-benzopyran-4-ones to 2,3-dihydro-1-benzofuran-3-carboxaldehydes or -carboxylic acid esters (6) have been reported previously. Oxidative rearrangement of enolizable ketones (5) with thallium(III)nitrate in trimethylorthoformate as taught by A. Mc Killop and E. C. Taylor (for a review see *Endavor*, 1976, 35, 88) and extended to ring contraction of benzopyran to benzolutah derivatives (S. Antus et al., *Chem. Ber.*, 1979, 112, 3879–3885 and G. Ciattini et al., *J Heterocycl. Chem.*, 1982, 19, 395–400). However, due to the simultaneous formation of other reaction products, the yields of rearranged product are generally poor. In applying this reaction to 6-hydroxy-substituted derivatives of 3,4-dihydro-1(2H)-benzopyran-4-ones (5) it is found that the choice of the protective group of these phenols greatly influences the yield of rearranged product. Thus, using the 6-acetoxy derivatives as starting materials, a 30–60% of rearranged product (with considerable difficulties in reproducibility) is obtained, the 6-benzyloxy derivative gave less than 10% of rearranged product. The use of 6-(p-nitrobenzoyl)oxy derivative 5 gave consistently good yields of 80–90% of 6 that is readily isolated without the need of chromatographic separation procedures. Thus, although thallium reagents have to be handled with great care because of their toxicity, the simplicity of the procedure and the high yields render this reaction suitable for large scale preparation of 2,3-dihydro-1-benzofuran derivatives that are otherwise not readily accessible.

REACTION SCHEME B

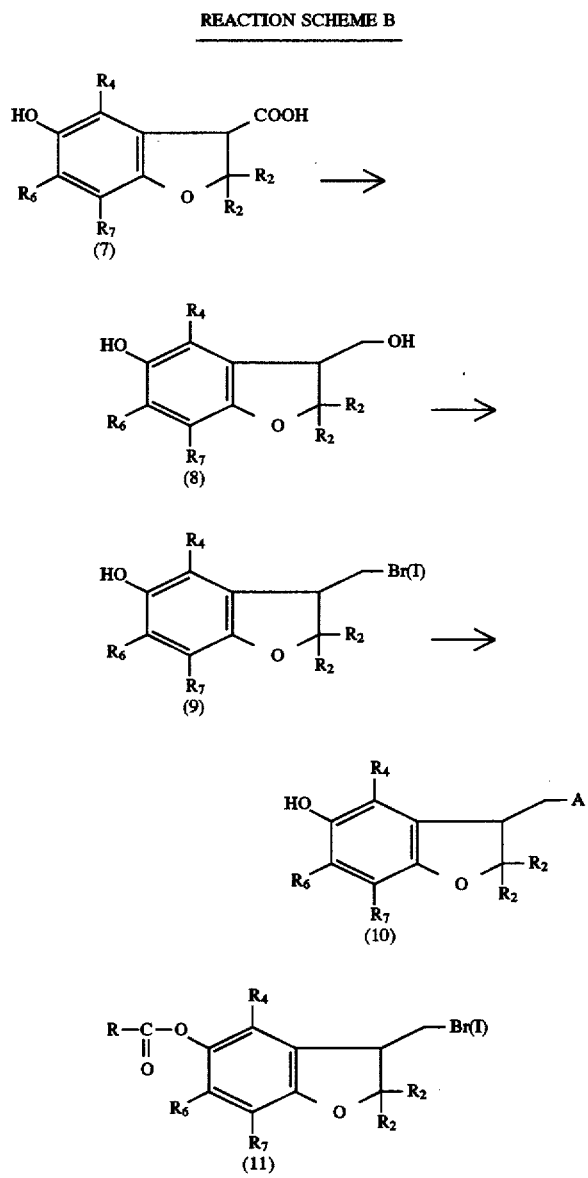

-continued
REACTION SCHEME B

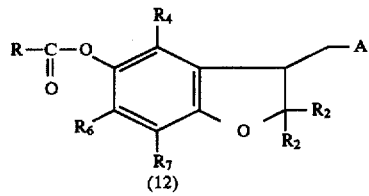

wherein $R, R_2, R_4, R_6, R_7$ and A are as previously defined.

The acids (7) can readily be reduced to the alcohols (8). Borane-dimethylsulfide complex is the preferred reagent for this reaction using tetrahydrofuran as solvent but other hydride reagents, such as lithium aluminum hydride can be used as well as other non-reactive solvents. Due to the steric hindrance which the 2,2-dialkyl substitution imparts, unusually long reaction times, preferably 16 to 48 hours, and elevated temperatures (reflux) are required. Conversion of the alcohols (8) to bromides (9) is best accomplished using bromotriphenylphosphonium bromide, obtained from triphenylphosphine and bromine in dichloromethane. The use of triphenylphosphine and tetrabromomethane in dimethylformamide gives less favorable results, even with extended reaction time. Conversion of the bromide to the iodide can be accomplished by refluxing it in acetonitrile with one equivalent of sodium iodide. Conversion of the bromides or iodides (9) to amine-substituted products (10) can be accomplished by procedures well known to the art, but again employing extended reaction time and elevated reaction temperatures to overcome steric hindrance. Thus, using dimethylformamide at 60°–80° C. or acetonitrile at reflux temperature the reaction of bromide (9) with an amine such as 1-methylpiperazine for 2 to 5 days will lead to acceptable yields of products (10). Protection of the phenolic hydroxy group by acylation to (11) is necessary in some instances, or desired in others, to obtain acylated products (12). The latter can also be obtained by acylation of (10) and the resulting products (11) may then be converted to compounds (12).

REACTION SCHEME C

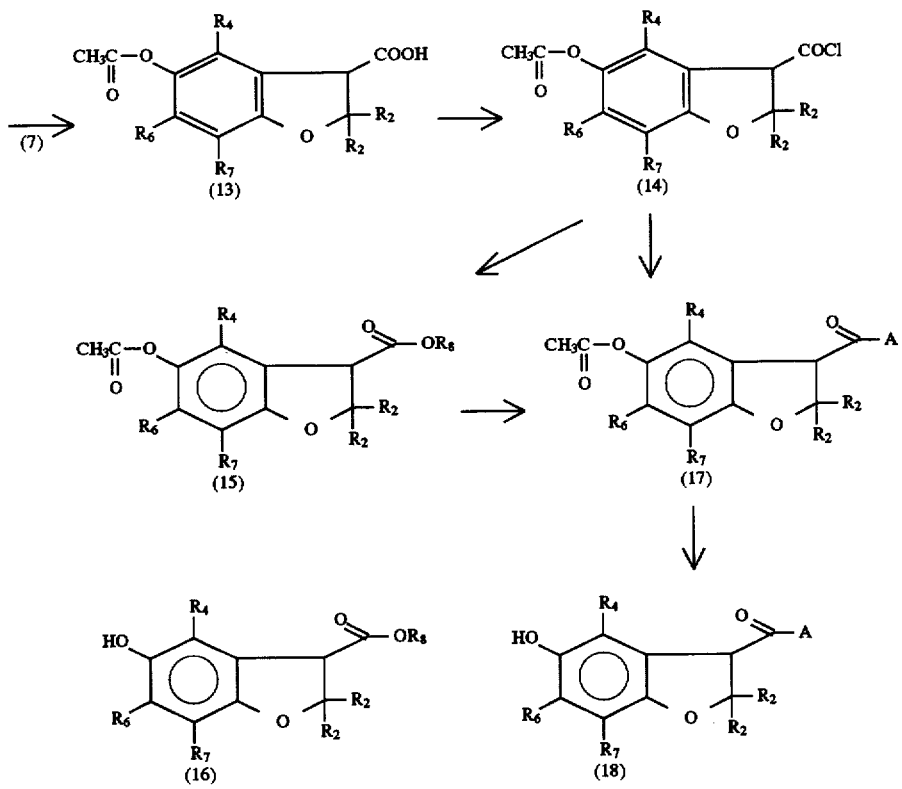

The acid (7), after protection of the phenolic hydroxy group to (13), can be converted to acid chlorides (14) using triphosgene (bistrichloromethyl carbonate) or diphosgene (trichloromethyl chloroformate) in the presence of triethylamine in an inert solvent, such as dichloromethane. Reaction of (14) with alcohols $HOR_8$, $R_8$ being as defined above, gives esters (15), which can be hydrolyzed selectively to (16) due to the steric hindrance of the 3-carboxylic ester group. Reaction of (14) with secondary or primary amines gives amides (17), which can be hydrolyzed to (18).

Further, as there is an asymmetric carbon atom at the 3-position, the compounds may occur as either the R— or the S-enantiomers, or mixtures thereof. The preparation of the individual enantiomeric form may be effected by resolving the acids of Formula (13) by standard and conventional means such as, for example, via the use of diastereomeric salts with optically active amines, or alternatively, by resolving the alcohols (8) as esters with optically active acids, e.g. L-2,4-MeClC$_6$H$_3$CHMeCOOH (Me representing methyl).

Having generically described the methods for the preparation of the compounds of this invention, the following examples describe the details of the processes and techniques involved.

EXAMPLE 1

2,3-DIHYDRO-5-HYDROXY-2,2,4,6,7-PENTAMETHYL-1-BENZOFURAN-3-CARBOXYLIC ACID

STEP A:

3,4-Dihydro-6-hydroxy-2,2,5,7,8-pentamethyl-2H-1-benzopyran-4-one

To 100 g of 3,3-dimethylacrylic acid is added 73 ml of thionyl chloride and the mixture is stirred for 2 hours at room temperature and for 1.5 hours at 110° C. Distillation at 40 mm gives 107.0 g (90%) of 3,3-dimethylacryloyl chloride, b.p. 66°–68° C. It is added to a solution of 68.68 g of trimethylhydroquinone in 500 ml of toluene and the mixture is slowly heated to reflux and stirred at that temperature for 1 hour. After cooling and addition of some ethyl ether the solution is washed with saturated sodium bicarbonate solution and is dried over sodium sulfate. Filtration and evaporation of solvent gives an oil that is crystallized from 780 ml of hexane to give 133.16 g (93%) of the bis-(3,3-dimethylacryloyl) ester of trimethylhydroquinone.

The ester is pulverized and mixed with 61.74 g (10% excess) of anhydrous aluminium chloride by means of a mechanical stirrer and heated to 135°–145° C. for 1.5 hours. The resulting melt is allowed to cool, dissolved in 200 ml of dichloromethane and 200 ml of 2N hydrochloric acid is added dropwise. The dichloromethane phase is separated, washed with sodium bicarbonate and a sodium chloride solution and dried over sodium sulfate. Filtration and evaporation of solvent gives an oil that is treated with 300 ml of methanol and 300 ml of 2N sodium hydroxide solution at reflux temperature for 1 hour. The mixture is cooled, acidified with 400 ml of 2N HCl and extracted twice with ethyl acetate. The extract is washed with water and sodium bicarbonate, dried over sodium sulfate, filtered and concentrated to about 300 ml. The product, 3,4-dihydro-6-hydroxy-2,2,5,7,8-pentamethyl-2H-1-benzopyran-4-one, crystallizes and is recrystallized from ethyl acetate to give 53.84 g. A second crop of 13.29 g raises the yield to 68%.

STEP B:

2,3-dihydro-5-(4-nitrobenzoyl)oxy-2,2,4,6,7-pentamethyl-1-benzofuran-3-carboxylic acid, methyl ester The p-nitrobenzoyl ester of this material (see Step A) is prepared by portionwise addition of 38.98 g of p-nitrobenzoyl benzoyl chloride to an ice-cooled solution of 46.86 g of 3,4-dihydro-6-hydroxy-2,2,5,7,8-pentamethyl-2H-1-benzopyran-4-one in 250 ml of pyridine and stirring at room temperature overnight. Water is added and the solid is collected and washed with water and a little methanol. Recrystallization from chloroform/methanol gives 74.62 g (97%).

A heterogeneous mixture of 30.20 g (0.079 mol) of 3,4-dihydro-6-(4-nitrobenzoyl)oxy-2,2,5,7,8-pentamethyl-2H-1-benzopyran-4-one, 36.86 g (0.083 m) of thallium (III) nitrate trihydrate, 200 ml of trimethylorthoformate, and 200 ml of methanol is stirred at room temperature for 4 days. The resulting solid is collected and washed with methanol. The residue is slurried in 100 ml of chloroform and filtered; this process is repeated three times. The combined filtrates are heated to boiling and the chloroform is gradually replaced by an equal volume of methanol until crystallization occurs to give 27.44 g (84%) of 2,3-dihydro-5-(4-nitrobenzoyl)oxy-2,2,4,6,7-pentamethyl-1-benzofuran-3-carboxylic acid, methyl ester, m.p. 215°–216° C. Elemental analysis, IR, UV, and $^1$H-NMR spectra confirm the structure. This procedure was scaled up to 402 g, and 380.9 g (87.8%) of product was obtained.

STEP C:

Methyl-2,3-Dihydro-5-hydroxy-2,2,4,6,7-pentamethyl-1-benzofuran-3-carboxylate

Treatment of a boiling solution of 20.67 g (0.05 mol) of this material (see Step B) in 200 ml of tetrahydrofuran with 50 ml of 2N sodium hydroxide for 1 hour is followed by evaporation of solvent (20 minutes), addition of water, and extraction with dichloromethane (three times). The extract is washed with water and a sodium chloride solution, dried over sodium sulfate, filtered and evaporated. The resulting solid is recrystallized from ethyl acetate/heptane to give 10.96 g (81%) of methyl 2,3-dihydro-5-hydroxy-2,2,4,6,7-pentamethyl-1-benzofuran-3-carboxylate, m.p. 145°–146° C. Elemental analysis, IR, UV, and $^1$H-NMR spectra confirm the structure.

STEP D:

2,3-Dihydro-5-hydroxy-2,2,4,6,7-pentamethyl-1-benzofuran-3-carboxylic acid

Refluxing 22.36 g of the above material (see Step C) in 100 ml of methanol and 100 ml of 2N sodium hydroxide for 24 hours is followed by acidification with 120 ml of 2N hydrochloric acid, evaporation of methanol, and extraction with ethyl acetate (twice). The extract is washed with water and acidic product is extracted into a sodium bicarbonate solution, which upon acidification is reextracted with ethyl acetate. The extract is dried over sodium sulfate, filtered and evaporated. The resulting solid is recrystallized from ethyl acetate/heptane to give 16.40 g (77%) of 2,3-dihydro-5-hydroxy-2,2,4,6,7-pentamethyl-1-benzofuran-3-carboxylic acid, m.p. 161°–164° C. Elemental analysis, IR, UV, and $^1$H-NMR spectra confirm the structure.

EXAMPLE 2

2,3-DIHYDRO-5-HYDROXY-2,2,4,6,7-PENTAMETHYL-1-BENZOFURAN-3-METHANOL

To a stirred solution of 58.82 g (0.235 mol) of 2,3-dihydro-5-hydroxy-2,2,4,6,7-pentamethyl-1-benzofuran-3-carboxylic acid (see Example 1) in 500 ml of dry tetrahydrofuran is added dropwise over 30 minutes 50 ml of 10M borane-methyl sulfide and the resulting mixture is stirred at reflux temperature for 7 hours. After cooling, 120 ml of methanol is added carefully and the resulting solution is evaporated to dryness. The residue is taken up in ethyl acetate and the solution is washed with 2N hydrochloric acid, water, a sodium bicarbonate solution, and brine, and is dried over anhydrous sodium sulfate. Filtration and evaporation of solvent gives an oil that crystallizes from ethyl acetate/heptane to give 37.85 g of the title compound, m.p. 89°–90° C. Elemental analysis, IR, UV, and $^1$H-NMR spectra confirm the structure. A second crop of 12.60 g is obtained, raising the yield to 91%.

EXAMPLE 3

3-BROMOMETHYL-2,3-DIHYDRO-2,2,4,6,7-PENTAMETHYL-1-BENZOFURAN-5-OL AND O-ACETATE

To an ice-cooled solution of 41.89 g (0.1595 mol=10% excess) of triphenylphosphine in 120 ml of 4A molecular sieve-dried dichloromethane is added dropwise a solution of 24.33 g (0,152 mol=5% excess) of bromine in 40 ml of dichloromethane. The resulting mixture is stirred at 0° C. for 1 hour (any remaining coloration by bromine is removed by additional addition of triphenylphosphine). To the bromotriphenylphosphonium bromide reagent thus prepared is added 34.26 g (0,145 mol) of 2,3-dihydro-5-hydroxy-2,2,4,6,7-pentamethyl-1-benzofuran-3-methanol and the resulting solution is stirred and allowed to warm up to room temperature for 18 hours. The solution is concentrated to a small volume and is chromatographed on silica gel using dichloromethane/hexane (1:2) as eluent. Fractions containing the product (as indicated by thin layer chromatography) are combined and evaporated to dryness to give 46.05 g. Crystallization from ethyl acetate/heptane gives a solid, m.p. 79°–80° C. Elemental analysis, IR, UV, and 1H-NMR spectra confirm the structure.

To a solution of 12.58 g of this material in 150 ml of pyridine is added 70 ml of acetic anhydride. After stirring at room temperature overnight, ice water is added and the resulting precipitate is collected, taken up in ethyl acetate, washed with 2N hydrochloric acid, water, a sodium bicarbonate solution, and brine, and dried over anhydrous sodium sulfate. Filtration and evaporation of solvent gives 13.30 g of the O-acetate of the title compound that crystallizes from ethyl acetate/heptane, m.p. 122°–123° C. Elemental analysis, IR, UV, and $^1$H-NMR spectra confirm the structure.

EXAMPLE 4

2,3-DIHYDRO-2,2,4,6,7-PENTAMETHYL-3-DIMETHYLAMINOMETHYl-1-BENZOFURAN-5-OL, HYDROCHLORIDE

Into 8 ml of dry dimethylformamide is bubbled dimethylamine gas until a volume of 10 ml is obtained. This solution is added to a solution of 4.98 g of 3-bromomethyl-2,3-dihydro-2,2,4,6,7-pentamethyl-1-benzofuran-5-ol (see Example 3) in 20 ml of dimethylformamide, and the stoppered mixture is stirred at room temperature for 7 days. Water and a sodium bicarbonate solution is added and the mixture is extracted with ethyl ether. The extract is washed twice with water and the basic product is separated by washing with 2N hydrochloric acid and water. These washes are basified by addition of solid sodium bicarbonate and reextracted into ethyl acetate. After drying over anhydrous sodium sulfate, filtration and evaporation, 2.80 g of an oil is obtained. This is dissolved in isopropanol and isopranolic hydrogen chloride is added to pH below 3. The resulting crystals are recrystallized from isopropanol to give 1.90 g of the title compound, m.p. 265°–267° C. (decomposition). Elemental analysis, IR, UV, and $^1$H-NMR spectra confirm the structure.

EXAMPLE 5

2,3-DIHYDRO-5-HYDROXY-N,N,N-2,2,4,6,7-OCTAMETHYL-1-BENZOFURAN-3-METHANAMINIUM 4-METHYLBENZENSULFONATE

A mixture of 4.28 g of 2,3-dihydro-2,2,4,6,7-pentamethyl-3-dimethylaminomethyl-1-benzofuran-5-ol (see Example 4) and 3.3 g (10% excess) of methyl 4-methylbenzenesulfonate in 60 ml of acetonitrile is refluxed for 18 hours. The solvent is evaporated and the residue is slurried in ethyl acetate. The resulting semi-solid is recrystallized twice from acetonitrile to give 3.7 g of the title compound, m.p. 244°–245° C. Elemental analysis, IR, UV, and $^1$H-NMR spectra confirm the structure.

EXAMPLE 6

2,3-DIHYDRO-2,2,4,6,7-PENTAMETHYL-3-(1-METHYLETHYLAMINO)-METHYL-1-BENZOFURAN-5-OL HYDROCHLORIDE

Following the procedure described in Example 4 but substituting dimethylamine by isopropylamine (10 equivalents) the title compound is obtained, m.p. 274°–276° C. (decomposition). Elemental analysis, IR, UV, and $^1$H-NMR spectra confirm the structure.

EXAMPLE 7

2,3-DIHYDRO-2,2,4,6,7-PENTAMETHYL-3-(1-PIPERIDINO)METHYL-1-BENZOFURAN-5-OL

Following the procedure described in Example 4 but substituting dimethylamine by piperidine (2 equivalents) the title compound is obtained, m.p. 273°–275° C. (decomposition).Elemental analysis, IR, UV, and $^1$H-NMR spectra confirm the structure.

EXAMPLE 8

2,3-DIHYDRO-2,2,4,6,7-PENTAMETHYL-3-(4-METHYLPIPERAZINO)METHYL-1-BENZOFURAN-5-OL DIHYDROCHLORIDE

A solution of 2.99 g of the compound described in Example 3 and 1.50 g of sodium iodide in 40 ml of acetonitrile is stirred at reflux temperature for 5 hours. After cooling, the mixture is filtered to remove sodium bromide that precipitates (0.81 g). To the filtrate is added 1.05 g of 1-methylpiperazine and the mixture is refluxed for 3 days. Sodium bicarbonate (1 equivalent) is added, the solvent is evaporated and the residue is taken up in ethyl acetate. The basic product is separated by washing with 2N hydrochloric acid and water, the washes are basified by addition of sodium bicarbonate, and the product is reextracted into ethyl acetate. After drying over anhydrous sodium sulfate, filtration and evaporation, 1.90 g of an oil is obtained. This oil is dissolved in isopropanol, and isopropanolic hydrogen chloride is added to pH below 3. The resulting crystals are recrystallized from isopropanol to give the title compound, m.p. 268°–269° C. (decomposition). Elemental analysis, IR, UV, and $^1$H-NMR spectra confirm the structure.

EXAMPLE 9

5-ACETOXY-2,3-DIHYDRO-2,2,4,6,7-PENTAMETHYL-3-(4-METHYLPIPERAZINOIMETHYL-1-BENZOFURAN DIACID MALEATE

To a solution of 1.90 g of the compound described in the preceding example (as free base) in 20 ml of pyridine is added 10 ml of acetic anhydride and the solution is stirred overnight. After addition of ice water and solid sodium bicarbonate (until no more carbon dioxide evolves) the product is extracted twice with ethyl acetate and the extract is washed with water and brine, and dried over anhydrous sodium sulfate. Filtration and evaporation of solvent gives an oil that is dried under high vacuum to remove traces of pyridine. The residue is dissolved in isopropanol and is added to a solution of 1.75 g of maleic acid in isopropanol. The resulting crystals are recrystallized from isopropanol to give the title compound, m.p. 172°–173° C. (decomposition). Elemental analysis, IR, UV, and $^1$H-NMR spectra confirm the structure.

EXAMPLE 10

2,3-DIHYDRO-3-[4-(2-HYDROXYETHYL)PIPERAZINO]METHYL-2,2,4,6,7-PENTAMETHYL-1-BENZOFURAN-5-OL DIACID MALEATE

A solution of 5.59 g of the compound described in Example 3 and 2.62 g of 1-(2-hydroxyethyl)piperazine in 40 ml of dry dimethylformamide is stirred at room temperature for 4 days and at 50° C. for 2 days. Water and 1 equivalent of sodium bicarbonate are added and the product is extracted into ethyl acetate. The basic product is separated by washing with 2N hydrochloric acid and water, the washes are made alkaline by addition of sodium bicarbonate and the product is reextracted into ethyl acetate (3.44 g). Addition to a solution of 4.64 g of maleic acid in isopropanol and recrystallization from isopropanol gives 4.7 g of the title compound, m.p. 113°–119° C. Elemental analysis, IR, UV, and $^1$H-NMR spectra confirm the structure.

EXAMPLE 11

5-ACETOXY-3-[4-(2-ACETOXYETHYL)PIPERAZINO]METHYL-2,3-DIHYDRO-2,2,4,6,7-PENTAMETHYL-1-BENZOFURAN DIACID MALEATE

Treating the compound described in the preceding example as free base with acetic anhydride in pyridine, as described in Example 9 gives the title compound, m.p.160°–162° C. (decomposition). Elemental analysis, IR, UV, and $^1$H-NMR spectra confirm the structure.

EXAMPLE 12

2,3-DIHYDRO-3-[4-[2-(2-HYDROXYETHOXY)ETHYL]PIPERAZINO]METHYL-2,2,4,6,7-PENTAMETHYL-1-BENZOFURAN-5-OL DIACID MALEATE

A mixture of 2.99 g of the compound described in Example 3, 1.83 g (5% excess) of 1-[2-(2-hydroxyethoxy)ethyl]piperazine, 1.50 g (1 equivalent) of sodium iodide and 0.84 g (1 equivalent) of sodium bicarbonate in 40 ml of acetonitrile is refluxed for 3 days. The solvent is evaporated and the residue is taken up in ethyl acetate and washed with water. The basic product is separated by washing with 2N hydrochloric acid and water, the washes are made alkaline by addition of sodium bicarbonate and reextracted with ethyl acetate. The extract is dried over anhydrous sodium sulfate, filtered and evaporated to give 2.85 g (73%) of product, which is then dissolved in isopropanol and is added to a solution of 2.32 g of maleic acid in isopropanol. The resulting crystals are recrystallized from isopropanol to give 3.34 g of the title compound, m.p. 124°–126° C. (decomposition). Elemental analysis, IR, UV, and $^1$H-NMR spectra confirm the structure.

EXAMPLE 13

2,3-DIHYDRO-2,2,4,6,7-PENTAMETHYL-3-[4-(2-PYRIMIDINYL)PIPERAZINO]METHYL-1-BENZOFURAN-5-OL ACID MALEATE

A solution of 2.61 g (0.011 mol) of 1-(2-pyrimidyl) piperazine dihydrochloride in 20 ml of water is made alkaline with a saturated potassium carbonate solution and the free base is extracted with toluene. The extract is evaporated and to the residue is added 2.99 g (0.01 mol) of the compound described in Example 3, 1.50 g (0.01 mol) of sodium iodide, 0.84 g (0.01 mol) of sodium bicarbonate and 50 ml of acetonitrile. The mixture is stirred at reflux temperature for 3 days. The solvent is evaporated and the residue is taken up in ethyl acetate and washed with water. The basic product is separated by washing with 2N hydrochloric acid and water, the washes are made basic by addition of sodium bicarbonate and reextracted with ethyl acetate. The extract is dried over sodium sulfate, filtered and evaporated. To the residue is added a solution of 2.32 g (0.02 mol) of maleic acid in isopropanol and the resulting crystals are recrystallized from isopropanol to give 3.5 g of the title compound, m.p. 161°–162° C. (decomposition). Elemental analysis, IR, UV, and $^1$H-NMR spectra confirm the structure.

EXAMPLE 14

2,3-DIHYDRO-2,2,4,6,7-PENTAMETHYL-3-[4-(PHENYLMETHYL)PIPERAZINO]METHYL-1-BENZOFURAN-5-OL DIACID MALEATE

Following the procedure described in Example 10, but substituting 1-(2-hydroxyethyl)piperazine by a molar equivalent of 1-benzylpiperazine results in the title compound, m.p. 134°–137° C. Elemental analysis, IR, UV, and $^1$H-NMR spectra confirm the structure.

EXAMPLE 15

2,3-DIHYDRO-2,2,4,6,7-PENTAMETHYL-3-[[2-(3,4-DIMETHOXYPHENYL)ETHYL]METHYLAMINO]METHYL-1-BENZOFURAN-5-OL ACID MALEATE

A solution of 2.99 g of the compound described in Example 3 and 1.50 g of sodium iodide in 40 ml of acetonitrile is refluxed overnight with stirring. The precipitated sodium bromide is removed by filtration and 1.95 g of N-methylbromoveratrylamine and 0.84 g of sodium bicarbonate is added to the filtrate. The resulting mixture is stirred at reflux temperature for 5 days. The solvent is evaporated and the residue is taken up in ethyl acetate and washed with water. The basic product is separated by washing with 2N hydrochloric acid and water, the washes are basified by addition of sodium bicarbonate and the product is reextracted into ethyl acetate. After drying over anhydrous sodium sulfate, filtration and evaporation, an oil is obtained, which is then dissolved in isopropanol and is added to a solution of 1.16 g of maleic acid in isopropanol. The resulting solid is recrystallized from isopropanol to give the title compound.

EXAMPLE 16

3-AMINOMETHYL-2,3-DIHYDRO-2,2,4,6,7-PENTAMETHYL-1-BENZOFURAN-5OL HYDROCHLORIDE

A mixture of 4.75 g of 5-acetoxy-3-bromomethyl-2,3-dihydro-2,2,4,6,7-pentamethyl-1-benzofuran (see Example 3) and 2.58 g (1 equivalent)of potassium phthalimide in 50 ml of dry dimethylformamide is stirred at 60° C. for 48 hours. Water is added and the product is extracted twice with ethyl ether. The extract is washed with water and brine, and is dried over anhydrous sodium sulfate. After filtration, evaporation of the solvent leaves a residue that is crystallized from ethyl acetate/heptane. The first crop contains free phthalimide, but subsequent crops yield 2,3-dihydro-2,2,4,6,7-pentamethyl-3-phthalimidomethyl-1-benzofuran-5-ol acetate.

A solution of this material in 50 ml of methanol and 50 ml of 2N sodium hydroxide is refluxed for 6 hours. After addition of 70 ml of 2N hydrochloric acid, methanol is removed by evaporation and the remaining aqueous phase is washed twice with ethyl acetate to remove non-basic product. The aqueous phase is made alkaline by addition of sodium bicarbonate and is extracted twice with ethyl acetate. The extract is dried over anhydrous sodium sulfate, filtered and evaporated. The residue is dissolved in ethyl ether and enough of ethereal hydrogen chloride is added to obtain a pH below 3. The hydrochloride salt is recrystallized from isopropanol/ethyl ether to obtain the title compound.

EXAMPLE 17

3R and 3S-Enantiomers of 5-ACETOXY-2,3-DIHYDRO-2,2,4,6,7-PENTAMETHYL-1-BENZOFURAN-3-CARBOXYLIC ACID To a solution of 25.03 g (0.1M) of 2,3-dihydro-5-hydroxy-2,2,4,6,7-pentamethyl-1-benzofuran-3-carboxylic acid (described in Example 1) in 200 ml of pyridine is added 100 ml of acetic anhydride and the mixture is stirred at room temperature for 24 hours. Water and ice is added and the mixture is stirred at about 30° C. for 30 minutes. More ice and 450 ml of 6N hydrochloric acid is added and the resulting solid is collected, washed with water, and taken up in ethyl acetate. The solution is washed with 2N hydrochloric acid and water and is dried over anhydrous sodium sulfate. The residue obtained after filtration and evaporation of solvent is recrystallized from ethyl acetate to give 23.6 g (81%) of the title compound as racemate, m.p. 187°–8° C. Elemental analysis, UV, and $^1$H-NMR spectra confirm the structure.

A solution of 15.27 g (0.0523M) of this material and 6.65 g (0.0523M) of S-(−)-α-methylbenzylamine in 100 ml of isopropanol, 2 ml of water and 300 ml of ethyl acetate is azeotroped to a volume of about 100 ml. The crystalline material obtained on cooling is recrystallized twice from the same solvent system to give 6.02 g (56%) of the diastereomeric salt, $\alpha^{25}_D = -13.81°$ (0.99% in $CH_3OH$), ee=99.5% by HPLC.

The combined filtrates are suspended in water, 50 ml of 2N hydrochloric acid is added and the acidic product is extracted twice with ethyl acetate. The extract is washed with 2N hydrochloric acid and sodium chloride solution, dried over anhydrous sodium sulfate, filtered and evaporated to give 11.34 g of an oil. To this is added 4.70 g (0.0388 m) of R-(+)-α-methylbenzylamine and crystallization results using the same solvent system. Two recrystallizations gave 7.90 g (73%) of the other diastereoisomeric salt, $\alpha^{25}_D = -14.21°$ (0.99% in $CH_3OH$), ee=99.1%. X-Ray crystallography shows this enantiomer to have the S-configuration.

EXAMPLE 18

3R-(+)- and 3S-(−)-ENANTIOMERS OF 2,3-DIHYDRO-2,2,4,6,7-PENTAMETHYL-3-(4-METHYLPIPERAZINO)-METHYL-1-BENZOFURAN-5-OL DIHYDROCHLORIDE HYDRATE The two diastereometric salts described in the preceding example are each converted to the free acid, reduced to the alcohols with borane-methyl sulfide, as described in Example 2, converted to the bromide, as described in Example 3, and allowed to react with 1-methylpiperazine as described in Example 8.

The enantiomer obtained from the R-acid is, by definition, the S-enantiomer of the title compound, $\alpha^{25}{}_D = -20.66°$ (1.67% in water, pH=1.3), ee=99.7% by HPLC. Elemental analysis, UV and $^1$H-NMR spectra confirm the structure. The enantiomer obtained from the S-acid is, by definition, the R-enantiomer of the title compound $\alpha^{25}{}_D = +20.68°$ (1.18% in water, pH=1.40), ee=99.7% by HPLC. Elemental analysis, UV and $^1$H-NMR spectra confirm the structure.

EXAMPLE 19

5-ACETOXY-2,3-DIHYDRO-2,2,4,6,7-PENTAMETHYL-1-BENZOFURAN-5-CARBOXYL CHLORIDE

To a solution of 9.59 g (0.047M) of trichloromethyl chloroformate in 80 ml of dry dichloromethane under nitrogen is added dropwise over 3 hours a solution of 13.75 g (0.047M) of 5-acetoxy-2,3-dihydro-2,2,4,6,7-pentamethyl-1-benzofuran-5-carboxylic acid (described in Example 17, racemate) and 4.77 g (0.847M) of triethylamine in 100 ml of dichloromethane. The escaping gas is trapped over potassium hydroxide. The mixture is stirred at room temperature overnight and at reflux temperature for 1 hour. The residue obtained after evaporation of solvent at 30° C. is suspended in toluene and the resulting precipitate of triethylamine hydrochloride is removed by filtration. The filtrate is evaporated and the residue is crystallized from hexane to give 10.93 g (75%) of the title compound, m.p. 171°–173.5° C. Elemental analysis, UV and $^1$H-NMR spectra confirm the structure. The identical product is obtained using bistrichloromethyl carbonate (triphosgene) instead of diphosgene in the above procedure.

EXAMPLE 20

2,3-DIHYDRO-5-HYDROXY-2,2,4,6,7-PENTAMETHYL-1-BENZOFURAN-3-CARBOXYLIC ACID ESTER with 1-(2-HYDROXYETHYL)-4-METHYLPIPERAZINE DIACID MALEATE To a solution of 3.48 g (0.0112M) of the acid chloride described in the preceding Example in toluene is added 1.62 g (0.0112M) of 4-methylpiperazin-1-ethanol, prepared from 4-methylpiperazine and ethylene oxide, and the mixture is refluxed overnight. After cooling the solution is washed with sodium bicarbonate solution, dried over anhydrous sodium sulfate, filtered and evaporated. The residue is refluxed in 50 ml of tetrahydrofuran and 25 ml of 2N sodium hydroxide for 45 minutes. After acidifying with 60 ml of 2N hydrochloric acid, the solution is washed with ethyl ether, sodium bicarbonate is added, and the product is extracted into ethyl acetate. The extract is dried over anhydrous sodium sulfate, filtered and evaporated and 2.60 g Of maleic acid is added to the residue in acetonitrile. Recrystallization from the same solvent gives 2.0 g of the title compound, m.p. 150°–154° C. Elemental analysis, UV and $^1$H-NMR spectra confirm the structure.

EXAMPLE 21

2,3-DIHYDRO-2,2,4,6,7-PENTAMETHYL-3-(4-METHYLPIPERAZINE-1-CARBOXY)-1-BENZOFURAN-5-OL ACID MALEATE

A solution of 4.22 g of the acid chloride described in Example 19 and 1.36 g of 1-methylpiperazine in 150 ml of toluene is refluxed for 4 hours. After cooling, the basic product is extracted into 2N hydrochloric acid, the solution is neutralized with sodium bicarbonate and the product is reextracted into ethyl acetate. The extract is dried over anhydrous sodium sulfate, evaporated, and the residue is crystallized from ethyl acetate/heptane to give 4.35 g (77%) of the O-acetate of the title compound, m.p. 171°–173.5° C. This material is refluxed in 25 ml of methanol and 25 ml of 2N sodium hydroxide for 45 minutes, methanol is evaporated and the residue is acidified with 2N hydrochloric acid. The resulting solution is washed with ethyl acetate, made basic with sodium bicarbonate and extracted with ethyl acetate. The extract is dried over anhydrous sodium sulfate, filtered and evaporated. One equivalent of maleic acid is added and the salt is crystallized and recrystallized from isopropanol/water to give the title compound, m.p. 227° C. (decomposition). Elemental analysis, UV and $^1$H-NMR spectra confirm the structure.

EXAMPLE 22

2,3-DIHYDRO-2,2,4,6,7-PENTAMETHYL-3-[4-(2-HYDROXYETHYL)PIPERAZINE-1-CARBOXY]-1-BENZOFURAN-5-OL ACID MALEATE

To 2.73 g (0.021M) of 1-(2-hydroxyethyl)piperazine in 50 ml of toluene is added 2.28 g (0.021M) of trimethylsilyl chloride. The solution is stirred for 3 hours at room temperature, washed with sodium bicarbonate solution, dried over anhydrous sodium sulfate and filtered. 6.22 g (0.02M) of the acid chloride described in Example 19 is added and refluxed for 5 hours. After cooling some ethyl acetate is added and the solution is washed with sodium bicarbonate solution, water, 2N hydrochloric acid and water. The acidic washes are neutralized with sodium bicarbonate and extracted with ethyl acetate. The extract is dried over anhydrous sodium sulfate, filtered and evaporated to give 5.20 g of an oil. To remove the silyl group 20 ml of 1M tetrabutylammonium fluoride in tetrahydrofuran is added, the solution is allowed to stand at room temperature overnight, the solvent is evaporated and the residue is taken up in ethyl acetate. The solution is washed with sodium bicarbonate solution, dried over anhydrous sodium sulfate, filtered and evaporated. To hydrolyze the O-acetate the residue is refluxed in 25 ml of methanol and 25 ml of 2N sodium hydroxide for 1 hour, methanol is evaporated and the residue is acidified with 2N hydrochloric acid. The resulting solution is washed with ethyl acetate, made basic with sodium bicarbonate and extracted with ethyl acetate. The extract is dried over anhydrous sodium sulfate, filtered and evaporated. One equivalent of maleic acid is added and the salt is crystallized and recrystallized from isopropanol/water/ethyl acetate to give 2.85 g (30%) of the title compound, m.p. 184°–5° C. (decomposition). Elemental analysis, UV and $^1$H-NMR spectra confirm the structure.

EXAMPLE 23

The compounds of the present invention can be tested for efficacy in stroke and nervous system trauma by the method described in *J. Neurosurgery* 62:882–887 (1985). Male CD-1 mice weighing 18–22 g are subjected to head injury produced by a 50 g weight dropped 32 cm. The neurological status is evaluated one hour later. Treatment of the mice with the compounds of interest can be pre-trauma or post-trauma. Improvement of neurological status of the treated mice shows efficacy. For testing efficacy in reperfusion injury, the compounds of the present invention can be tested according to the method described in *Stroke* 20:1037–1043 (1989).

Male Sprague-Dawley rats weighing 250–300 g are subjected to occlusion of middle cerebral artery followed by reperfusion. Reduction of infarct size shows efficacy in the treated rats.

The compounds of this invention are free radical scavengers. Free radical reactions have been implicated in the pathology of more than 50 human diseases. Radicals and other reactive oxygen species are formed constantly in the human body both by deliberate synthesis (e.g. by activated phagocytes) and by chemical side-reactions. They are removed by enzymic and non-enzymic antioxidant defence systems. Oxidative stress, occurring when antioxidant defences are inadequate, can damage lipids, proteins, carbohydrates and DNA. A few clinical conditions are caused by oxidative stress, but more often the stress results from the disease and can make a significant contribution to the disease pathology. For a more detailed review see B. Halliwell in Drugs, 1991, 42, 569–605.

There is a growing body of information that suggests a pathophysiologic role of oxygen free-radical-mediated lipid peroxidation following central nervous system trauma or stroke, either ischemic or haemorrhagic. A reduction in cerebral tissue concentration of endogenous antioxidants has been observed, as well as an increase in lipid peroxidation products. Inhibitors of brain lipid peroxidation counteract and reduce cerebral tissue damage, as well as to prolong life of traumatized animals. These findings have been reviewed by E. D. Hall and J. M. Braughler in Free Radical Biology and Medicine, 1989, 6, 303–313 and elsewhere. M. Miyamoto et al., (J. Pharmacol. Exp. Ther., 1989, 250, 1132) report that neurotoxicity due to excessive glutamic acid release is similarly reduced by antioxidants. They suggest the use of agents that inhibit brain lipid peroxidation for treatment of neurodegenerative diseases such as Huntington's and Alzheimer's disease in which excessive glutamic acid release has been observed. M. R. Hori et al., (Chem. Pharm. Bull. 1991, 39, 367) report on anti-amnesic activity of brain lipid peroxidation inhibitors in rats.

The role of oxygen free radicals in Parkinson's disease has been reviewed recently (Free Radical Biol. Med., 1991, 10, 161–169) and a free radical scavenger has been tested clinically with some success (Fundam. Clin. Pharmacol., 1988, 2, 1–12).

Ischemia followed by reperfusion causes formation of oxygen-derived free radicals and increased lipid peroxidation and results in tissue injury. Administration of free radical scavengers to animals subjected to ischemia/reperfusion reduces these effects in heart, lung, kidney, pancreas, brain and other tissues.

The compounds of the present invention are also useful in treating the process of inflammation which is known to involve the release of superoxide radicals from phagocytic cells which cause some of the symptoms of rheumatoid arthritis and other inflammatory diseases such as ulcerative colitis. Inhalation injury of the lungs is typically caused by heat and chemical irritation, and chemical injury is the leading lethal cause of smoke inhalation injury. Smoke inhalation leads to lung injury due to an increase in pulmonary microvasculature and pulmonary edema. This process is accompanied by increased lipid peroxidation in lung tissue. An inhibitor of lipid peroxidation was shown to reduce these symptoms in animals subjected to hot sawdust smoke by Z. Min et al., (J. Med. Cell PLA, 1990, 5, 176–180). They suggest the use of antioxidants in treatment of smoke inhalation-lung injury, adult respiratory distress syndrome and emphysema.

Reactive oxygen species also play a role in the formation of foam cells in atherosclerotic plaques (reviewed by D. Steinberg et al., New Engl. J. Med., 1989, 320, 915–924) and the free radical scavenger probucol has a marked antiatherosclerotic effect in hyperlipidemic rabbits (Carew et al., Proc. Nat. Acad. Sci. USA, 1987, 84, 7725–7729. Degenerative retinal damage and diabetogenic retinopathy have also been listed as target for treatment with free radical scavengers (cf. J. W. Baynes, Diabetes, 1991, 40, 405–412; S. P. Wolff et al., Free Rad. Biol. Med., 1991, 10, 339–352.

The compounds may also be useful in the treatment of cancers, and degenerative diseases related to aging, stroke, and head trauma, since oxygen-derived free radicals have been identified among causative factors. For reviews, see B. Halliwell and C. Gutteridge, Biochem. J., 1984, 219, 1–14; TINS 1985, 22–6. Antioxidants have also been shown to be useful in the treatment of cataracts, Free Rad. Biol. Med., 12:251–261 (1992).

In vitro and in vivo activity for the compounds of this invention may be determined by the use of standard assays which demonstrate the free radical scavenging property, affinity for cardiac tissue and cardioprotective properties, as well as by comparison with agents known to be effective for these purposes.

Exemplary of the assay useful for determining the free-radical scavenging property of the compounds of this invention is by the in vitro inhibition of lipid peroxidation in rat brain homogenates.

The free radical scavenging properties of the compounds may readily be evaluated in an assay wherein superoxide radicals are generated by 4 mU of xanthine oxidase in the presence of 0.1 mM xanthine and detected by reduction of 40 µM nitro blue tetrazolium (NBT) to the diformazan dye in a spectrophotometric assay as described by C. Beauchamp and I. Fridovick, (Analyt. Biochem. 1971, 44, 276–287). 30 U of superoxide dismutase inhibited this reduction by 90% which is due to superoxide radicals. In the presence of a superoxide scavenger (test compound) there is a competition for the superoxide radical and thus a reduction in the color formation of NBT demonstrates the superoxide radical scavenging property of the test compound.

Inhibiting the process of lipid peroxidation may be assayed using tissue homogenates for measuring the antioxidant activity of biological fluids by the methodology of J. Stocks et al., (Clin. Sci. Mol. Med., 1974, 47, 215–222), wherein a brain tissue homogenate of treated adult Sprague Dawley rats is utilized.

Samples of total volume 1 ml of diluted brain homogenate and with the scavenger at an appropriate dilution are incubated. Non-incubated samples are taken as background. Controls are run without scavenger and a sample containing only buffer is taken as blank. After incubation at 37° C. for 30 minutes, 200 µl of 35% perchloric acid is added, the samples centrifuged and 800 µl of the supernatants mixed with 200 µl of 1% thiobarbituric acid. The pink condensation product of thiobarbituric acid reactive material is developed at 100° C. in a boiling water bath for 15 minutes, and absorbance read at 532 nm.

For ex vivo inhibition of tissue including heart or brain tissue, lipid peroxidation in mice may be utilized to demonstrate the ability of the compounds to penetrate and act as free radical scavengers in these tissues. This assay involves pretreatment of male CD1 mice by subcutaneous administration of the test compound. One hour later the tissues are excised, homogenized 1+9 (w/v) in 20 mM potassium phosphate buffer at pH 7.3 (0.14M KCl) and incubated at 1/100 concentration in 1 ml of buffer at 37° C. for 30–120 minutes. At the end of the incubation 200 µl of 35% perchloric acid is added and proteins removed by centrifugation. To 800 ml of the supernatant are added 200 µl of 1% TBA and the samples are treated to 100° C. for 15 minutes. The TBA-adduct is extracted into 2 times 1 ml of n-butanol. The fluorescence is measured at an excitation wavelength of 515 nm and an emission wavelength of 553 nm against a standard prepared from malondialdehyde dimethylacetal.

Stimulated human leukocytes release radicals and other oxygen metabolites, which, during inflammation, act as microbicidal agents. At the same time, they release proteolytic enzymes, such as elastase, which are also microbicidal but potentially threaten the connective tissue of the host. An endogenous $\alpha_1$-proteinase inhibitor ($\alpha_1$Pi) normally protects the host tissue from proteolytic digestion. $\alpha_1$Pi is however, inactivated by the leukocyte-derived oxidants. Antagonism of the of $\alpha_1$Pi is an indication of the disclosed radical scavengers. The concentration needed to protect 50% of the elastase inhibitory capacity of $\alpha_1$Pi ($PC_{50}$) depends on the amount of stimulated leukocytes present.

Method: The procedure described by Skosey and Chow was followed (see J. L. Skosey and D. C. Chow in *Handbook of Methods for Oxygen Radical Research* (Greenwald, R. A., ed.) 1985, pp. 413–416, CRC Press, Boca Raton). In short, human $\alpha_1$Pi was incubated with zymosan-stimulated human peripheral-blood leukocytes in the absence or presence of the scavengers. The amount of $\alpha_1$Pi protected from oxidative inactivation was determined by its residual elastase inhibitory capacity.

The relevance to inflammation matter has been reviewed by Weiss (see S. J. Weiss, *N. England J. Med.*, 1989, 320, 365–376). Lung emphysema is associated with a genetic defect in $\alpha_1$Pi; the disease is further enhanced by oxidants inhaled during cigarette smoking, which leads to oxidative inactivation of $\alpha_1$Pi in the lung tissue (see J. Travis and G. S. Salvesen, *Annu. Reu. Biochem.*, 1983, 52, 655–709). Oxidized $\alpha_1$Pi has also been isolated from rheumatoid synovial fluid (see P. S. Wong and J. Travis, *Biochem. Biophys. Roc. Commun.*, 1980, 06, 1440–1454). The degradation of hyaluronic acid, a macromolecule accounting for the viscosity of synovial fluid, is triggered by superoxyl radicals released from human leukocytes in vitro (see R. A. Greenwald and S. A. Moak, *Inflammation*, 1986, 10, 15–30). Furthermore, nonsteroidal anti-inflammatory drugs were shown to inhibit the release of superoxyl radicals from leukocytes (see H. Strom and I. Ahnfelt-Ronne, *Agents and Actions*, 1989, 26, 235–237 and M. Roch-Arveiller, V. Revelant, D. Pharm Huy, L. Maman, J. Fontagne, J. R. J. Sorenson and J. P. Giroud, *Agents and Actions*, 1990, 31, 65–71), and 5-aminosalicylic acid may exert its therapeutic activity in inflammatory bowel disease by a radical scavenger mechanism (see L Ahnfelt-Ronne, O. H. Nielsen, A. Christensen, E. Langholz, V. Binder and P. Riis, *Gastroenterology*, 1990, 98, 1162–1169). Therefore, it is believed that the compounds of this invention may be useful in the mentioned pathologic situations and that inflammatory bowel disease may be a special target. An immune stimulatory effect of antioxidants has also been reported in that they enhanced lymphocyte activity (R. Anderson and P. T. Lukey, *Ann. N.Y Acad. Sci.*, 1987, 498, 229–247) in vitro in the presence of triggered leukocytes, and ex vivo after pretreatment of human volunteers.

Thus, using standard and well known methodology, as well as by comparison with known compounds found useful, it is to be found that the compounds are free radical scavengers useful in the prevention and treatment of such disease states related to neurotoxicity due to excessive glutamic acid release, to Huntington's disease, Alzheimer's disease and other cognitive dysfunctions, (e.g. memory, learning and attention deficits), amnesia, and Parkinson's disease, as well as the treatment and prevention of tissue damage in heart, lung, kidney, pancreas and brain tissues induced by ischemia/reperfusion, and to allay acute blood loss due to haemorrhagic shock.

The compounds of the present invention are of particular interest in treating patients with stroke, nervous system trauma, and reperfusion damage. As used herein, these terms have the following meanings:

a) stroke means cerebrovascular disease which includes cerebral insufficiency due to transient disturbances of blood flow, infarction, and arteriovenous malformation which causes symptoms of mass lesion, infarction, or hemorrhage.

b) nervous system trauma means injury to the head or spine. For example, injury can occur from skull or spine penetration or from rapid brain acceleration or deceleration which injures tissue at the point of impact, at its opposite pole or within the frontal or temporal lobes. Injury may consist of nerve tissue, blood vessels and/or meninges damage resulting in neural disruption, ischemia and/or edema.; and c) reperfusion damage means the damage that occurs in any blood-deprived tissue, anywhere in the body, upon reintroduction of the blood supply. For example, reperfusion of an ischemic area of the myocardium or the cerebrum.

The compounds of this invention can be utilized both prophylactically and therapeutically. The amount of active ingredient for therapeutic administration can vary over a wide range and is dependent upon such factors as the species of patient to be treated, its age, health, sex, weight, nature and the severity of the condition being treated. The term "patient" refers to a warm-blooded animal such as, for example, rats, mice, dogs, cats, guinea pigs, primates and humans. Generally, a therapeutically effective amount of the active ingredient to be administered will range from about 0.1 mg/kg to 30 mg/kg of body weight per day. For prophylactic administration, corresponding lower doses can be utilized. Preferably, the compounds of the present invention will be administered to the patient in combination with a pharmaceutically acceptable carrier which is any substance which aids in the administration of the compound without substantially affecting its therapeutic properties.

Most preferably, the compounds are administered intravenously particularly under crisis situations wherein it is essential that the therapeutic agent be gotten to its site of action as quickly as possible, such as in those emergency conditions caused by coronary infraction, stroke and surgical interventions, conditions which can cause severe reperfusion damage.

The compounds of this invention also can be orally administered, preferably using more active ingredient per day than when parenterally administered, preferably taking divided doses 3 to 4 times per day. Preferably, enteral administration in post "crisis" situations, particularly after release from hospitalized conditions. The compounds can be used in standard dosage unit forms such as tablets, capsules, dragees, lozenges, elixirs, emulsions, suspensions, and in cases wherein topical application is preferred by suppository or sub-lingual administration. Tablets and capsules containing from 100 to 400 mg of active ingredient are preferred modes of enteral administration. Of course, in the treatment of inflammation the preferred method of administration is by depot injection directly to the situs of the inflammation area with follow-up enteral means of administration.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet granulations and which prevent adhesion of tablet material to the surfaces of tablet dies and punches. Suitable lubricants include, for example, talc stearic acid, calcium stearate, magnesium stearate and zinc stearate. Also included within the definition of a pharmaceutical carrier as used herein, are disintegrating agents added to assist the breakup and dissolution of tablets following administration, as well as coloring and/or flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene glycols, either with or without the addition of a surfactant. In general, the preferred liquid excipients, particularly for injectable preparations, include water, physiological and saline solutions, dextrose and glycol solutions such as an aqueous propylene glycol or polyethylene glycol solutions. In order to minimize or eliminate irritation at the site of injection, such compositions may contain a non-ionic surfactant having a hydrophile-lipophile balance (BLB) of from about 12 to about 17. The quantity of surfactant in such formulations ranges from about 5 to 15% by weight. The surfactant can be a single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. In certain topical and paten fetal preparations, various oils can be utilized as carriers or excipients. Illustrative of such oils are mineral oils, glyceride oils such as lard oil, cod liver oil, peanut oil, sesame oil, corn oil and soybean oil. For insoluble compounds, suspending agents may be added as well as agents to control the viscosity, as for example, magnesium aluminum silicate or carboxymethylcellulose. In addition to these excipients, buffers, preservatives and emulsifying agents may also be added. Typical enema preparation of the retention type enema utilizes small volumes, generally much less than about 150 mL for an adult, typically volumes of only a few milliliters are preferred. Excipients and solvents for use in retention anemas should, of course, be selected so as to avoid colonic irritation and should also be selected so as to minimize absorption of the various agents.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The compounds of the present invention may be incorporated into an aerosol preparation by means commonly known to those skilled in the art. The aerosol preparation may be prepared for use as a topical aerosol or may be prepared for inhalation. The aerosol preparation may be in the form of a solution or suspension and may contain other ingredients such as solvents, propellants and/or dispersing agents. Typical examples of aerosol preparations are shown in *Remington's Pharmaceutcal Sciences*, 18th ed., Mack Publishing Company, Easton Pa., pp. 1694–1712 (1990) incorporated herein by reference.

As it is true for most classes of compounds suitable for use as therapeutic agents certain subclasses and certain specific compounds are more preferred than others. In this instance it is preferred that the $R_2$, $R_4$, $R_6$ and $R_7$ moieties be methyl. Preferably $R_5$ is H or an acyl moiety including formyl and acetyl. X is preferably $CH_2A$. A is preferably

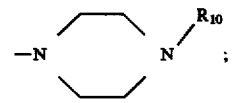

$R_{10}$ is preferably $C_{1-6}$ alkyl, more preferably $C_{1-3}$ alkyl and most preferably methyl. Other preferred forms of $R_{10}$ are acyloxyalkylene, especially —$CH_2$—O—$C(O)CH_3$, hydroxyalkyl ($C_{2-6}$) especially $(CH_2)_2$—OH, and pyrimidinyl.

What is claimed is:

1. A compound of the formula

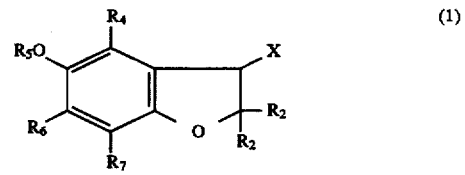

(1)

stereoisomer or mixture thereof, or their pharmaceutically acceptable salts thereof, wherein $R_2$ is $C_{1-4}$ alkyl or both $R_2$ moieties, when taken together with the carbon atom to which they are attached, form a $C_{5-6}$ cyclic hydrocarbyl moiety;

$R_4$ is $C_{1-6}$ alkyl $R_5$ is H or —C(O)R with R being H, or $C_{1-9}$ alkyl;

$R_6$ is $C_{1-6}$ alkyl;

$R_7$ is H or $C_{1-6}$ alkyl;

X is —$CH_2A$;

A is pyrrolidino, piperidino morpholino, or

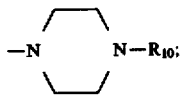

$R_{10}$ is H, $C_{1-8}$alkyl, $C_{2-6}$ alkenyl, $C_{4-6}$ cycloalkyl, cyclohexylmethyl, hydroxyalkyl ($C_{2-6}$), dihydroxyalkyl ($C_{3-6}$), $C_{2-9}$ acyloxyalkyl ($C_{2-6}$), $C_{1-4}$ alkoxyalkyl ($C_{1-6}$), —$(CH_2)_{2-6}$—O—$(CH_2)_{2-4}$ OH, pyrimidyl or

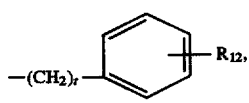

with t being 0, 1, or 2; and $R_{12}$ is ortho $C_{1-4}$ alkoxy, ortho $C_{1-4}$ alkyl or p-halo.

2. The compound of claim 1 wherein each $R_2$ are methyl.
3. The compound of claim 1 wherein $R_4$ is methyl.
4. The compound of claim 1 wherein $R_5$ is hydrogen.
5. The compound of claim 1 wherein $R_6$ is methyl.
6. The compound of claim 1 wherein A is

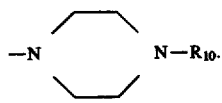

7. The compound of claim 6 wherein $R_{10}$ is methyl.
8. The compound of claim 1 wherein $R_7$ is methyl.
9. The compound of claim 1 wherein each $R_2$ are $C_{1-4}$alkyl, $R_5$ is hydrogen, $R_7$ is $C_{1-6}$alkyl and A is

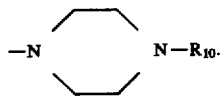

10. The compound of claim 9 wherein $R_{10}$ is $C_{1-8}$alkyl.
11. The compound of claim 9 wherein $R_{10}$ is methyl.
12. The compound of claim 1 wherein the compound is 2,3-Dihydro-2,2,4,6,7-pentamethyl-3-(1-piperidino)methyl-1-benzofuran-5-ol or pharmaceutically acceptable salts thereof.
13. The compound of claim 1 wherein the compound is 2,3-Dihydro-2,2,4,6,7-pentamethyl-3-(4-methylpiperazino)methyl-1-benzofuran-5-ol or pharmaceutical salts therof.
14. The compound of claim 1 wherein the compound is 5-Acetoxy-2,3-dihydro-2,2,4,6,7-pentamethyl-3-(4-methylpiperazino)methyl-1-benzofuran or pharmaceutically acceptable salts thereof.
15. The compound of claim 1 wherein the compound is 2,3-Dihydro-3-[4-(2-hydroxyethyl)piperazino]methyl-2,2,4,6,7-pentamethyl-1-benzofuran-5-ol or pharmaceutically acceptable salts thereof.
16. The compound of claim 1 wherein the compound is 5-Acetoxy-3-[4-(2-acetoxyethyl)piperazino]methyl-2,3-dihydro-2,2,4,6,7-pentamethyl-1-benzofuran or pharmaceutically acceptable salts thereof.
17. The compound of claim 1 wherein the compound is 2,3-Dihydro-3-[4-[2-(2-hydroxyethoxy)ethyl]piperazino]methyl-2,2,4,6,7-pentamethyl-1-benzofuran-5-ol or pharmaceutically acceptable salts thereof.
18. The compound of claim 1 wherein the compound is 2,3-Dihydro-2,2,4,6,7-pentamethyl-3-[4-(2-pyrimidinyl)piperazino]methyl-1-benzofuran-5-ol or pharmaceutically acceptable salts thereof.
19. The compound of claim 1 wherein the compound is 2,3-Dihydro-2,2,4,6,7-pentamethyl-3-[4-phenylmethyl)piperazino]methyl-1-benzofuran-5-ol or pharmaceutically acceptable salts thereof.
20. The compound of claim 1 wherein the compound is 3R-(+)-enantiomer of 2,3-Dihydro-2,2,4,6,7-pentamethyl-3-(4-methylpiperazino)methyl-1-benzofuran-5-ol or pharmaceutically acceptable salts thereof.
21. The compound of claim 1 wherein the compound is 3S-(−)-enantiomer of 2,3-Dihydro-2,2,4,6,7-pentamethyl-3-(4-methylpiperazino)methyl-1-benzofuran-5-ol or pharmaceutically acceptable salts thereof.
22. A pharmaceutical composition comprising a compound of claim 1 and a pharmaceutically acceptable carrier.
23. A method of treating a patient for reperfusion damage by administering an effective amount of a compound of claim 1.
24. A method of treating a patient for stroke by administering an effective amount of a compound of claim 1.
25. A method of treating a patient for nervous system trauma by administering an effective amount of a compound of claim 1.
26. The process of making a compound of the formula

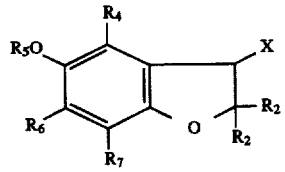

(1)

stereoisomer or mixture thereof, or their pharmaceutically acceptable salts thereof, wherein $R_2$ is $C_{1-4}$ alkyl or both $R_2$ moieties, when taken together with the carbon atom to which they are attached, form a $C_{5-6}$ cyclic hydrocarbyl moiety;

$R_4$ is $C_{1-6}$ alkyl;

$R_5$ is H or —C(O)R with R being H, or $C_{1-9}$ alkyl;

$R_6$ is $C_{1-6}$ alkyl;

$R_7$ is H or $C_{1-6}$ alkyl;

X is —$CH_2A$;

A is pyrrolidino, piperidino morpholino, or

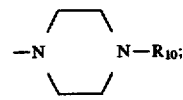

$R_{10}$ is H, $C_{1-8}$alkyl, $C_{2-6}$ alkenyl, $C_{4-6}$ cycloalkyl, cyclohexylmethyl, hydroxyalkyl ($C_{2-6}$), dihydroxyalkyl ($C_{3-6}$), $C_{2-9}$ acyloxyalkyl ($C_{2-6}$), $C_{1-4}$ alkoxyalkyl ($C_{1-6}$), —$(CH_2)_{2-6}$—O—$(CH_2)_{2-4}$ OH pyrimidyl or

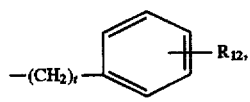
with t being 0, 1, or 2; and
$R_{12}$ is ortho $C_{1-4}$ alkoxy, ortho $C_{1-4}$ alkyl or p-halo by reacting the compound
(5')
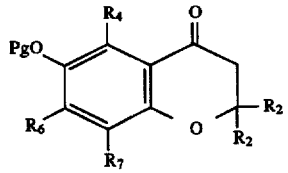
wherein Pg is $C_{1-9}$ alkyl, $C(O)C_{1-9}$ alkyl, aryl or $C(O)$ aryl with thallium(III)$(NO_3)_3$ 3 $H_2O$ in $(CH_3)O_3CH$ and $CH_3OH$ to produce
(6')
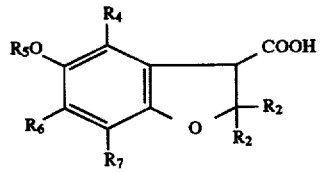
which is hydrolyzed to produce
(7')
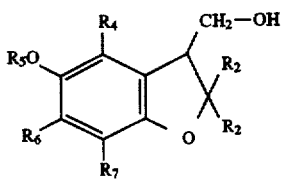
which is reduced to produce
(8')
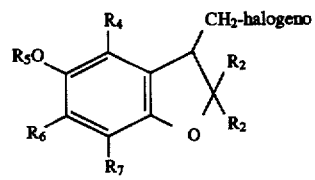
which is halogenated to produce
(9')
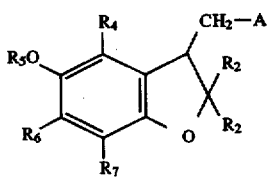
which is aminated to produce
(10')
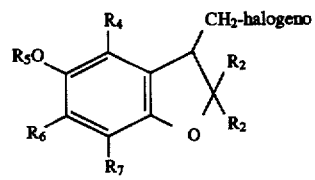
* * * * *

UNITED STATES PATENT AND TRADEMARK OFFICE
CERTIFICATE OF CORRECTION

PATENT NO. : 5,721,233

DATED : 24 February 1998

INVENTOR(S) : J. Martin Grisar, et al.

It is certified that error appears in the above-indentified patent and that said Letters Patent is hereby corrected as shown below:

Column 2, Line 4 patent reads: "R is B" and should read --- R is H .

Column 4, Line 51 patent reads "benzolutah" and should read --- benzofuran.

Column 8, Line 44 patent reads "780" and should read --- 700.

Column 10, Line 24 patent reads "(0,145 mol)" and should read --- (0.145 mol).

Column 10, Line 33 patent reads "1H-NMR" and should read --- $^1$H-NMR.

Column 13, Line 63 patent reads "-5OL" and should read --- -5-OL.

Column 15, Line 23 patent reads "(0.847M) and should read --- (0.047 M).

Column 15, Line 55 patent reads "Of" and should read --- of.

UNITED STATES PATENT AND TRADEMARK OFFICE
CERTIFICATE OF CORRECTION

PATENT NO. : 5,721,233
DATED : 24 February 1998
INVENTOR(S) : J. Martin Grisar, et al.

It is certified that error appears in the above-indentified patent and that said Letters Patent is hereby corrected as shown below:

Column 21, Line 29 patent reads "(BLB)" and should read --- (HLB).

Column 21, Line 39 patent reads "paten fetal" and should read --- parenteral.

Signed and Sealed this

Twelfth Day of October, 1999

Q. TODD DICKINSON

*Attest:*

*Attesting Officer*   Acting Commissioner of Patents and Trademarks